(12) United States Patent
Toyoda

(10) Patent No.: US 6,647,782 B2
(45) Date of Patent: Nov. 18, 2003

(54) CAPACITIVE HUMIDITY SENSOR

(75) Inventor: Inao Toyoda, Anjo (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 10/194,305

(22) Filed: Jul. 15, 2002

(65) Prior Publication Data

US 2003/0010119 A1 Jan. 16, 2003

(30) Foreign Application Priority Data

Jul. 16, 2001 (JP) ........................................ 2001-215655

(51) Int. Cl.[7] ........................... G01N 27/22; H01G 7/00; H01G 5/20
(52) U.S. Cl. ................ 73/335.04; 73/29.05; 73/335.02; 361/286; 257/253
(58) Field of Search ................... 73/335.04, 335.02, 73/335.03, 29.05; 257/252, 253; 361/286; 329/71.1

(56) References Cited

U.S. PATENT DOCUMENTS

| 4,057,823 | A | * | 11/1977 | Burkhardt et al. | .......... 257/414 |
|---|---|---|---|---|---|
| 4,277,742 | A | * | 7/1981 | Kovac et al. | ................ 324/689 |
| 4,305,112 | A | | 12/1981 | Heywang et al. | ......... 73/335.04 |
| 4,816,888 | A | * | 3/1989 | Tanaka et al. | ................ 257/253 |
| 4,893,214 | A | * | 1/1990 | Nishiwaki et al. | ........... 361/286 |
| 5,050,434 | A | * | 9/1991 | Demisch | ................... 73/335.04 |
| 5,075,816 | A | * | 12/1991 | Stormbom | .................... 361/286 |
| 5,345,213 | A | * | 9/1994 | Semancik et al. | ............. 338/34 |
| 6,111,280 | A | * | 8/2000 | Gardner et al. | .............. 257/253 |

FOREIGN PATENT DOCUMENTS

| GB | 2149922 A | 6/1985 | |
|---|---|---|---|
| JP | 58151549 A | * 9/1983 | .............. 73/335.02 |
| JP | B2-6-105235 | 12/1994 | |
| JP | A-9-127260 | 5/1997 | |
| WO | WO-01/42776 A1 | * 9/2000 | |

* cited by examiner

Primary Examiner—Edward Lefkowitz
Assistant Examiner—Michael Cygan
(74) Attorney, Agent, or Firm—Posz & Bethards, PLC

(57) ABSTRACT

A humidity sensor has two detection electrodes located on a semiconductor substrate and a humidity sensitive film. The capacitance of the film changes in response to humidity. The sensor includes a reference capacitor and a feedback capacitor. An electrode of each capacitor is located beneath one of the detection electrodes to limit the size of the device.

12 Claims, 10 Drawing Sheets

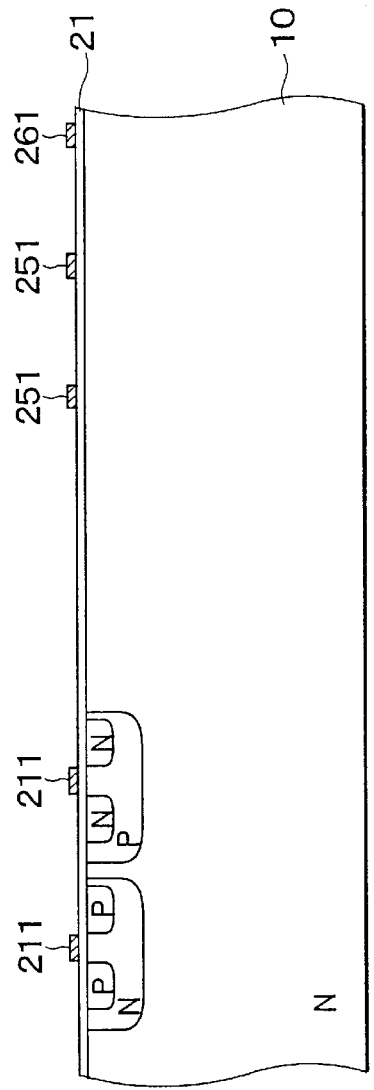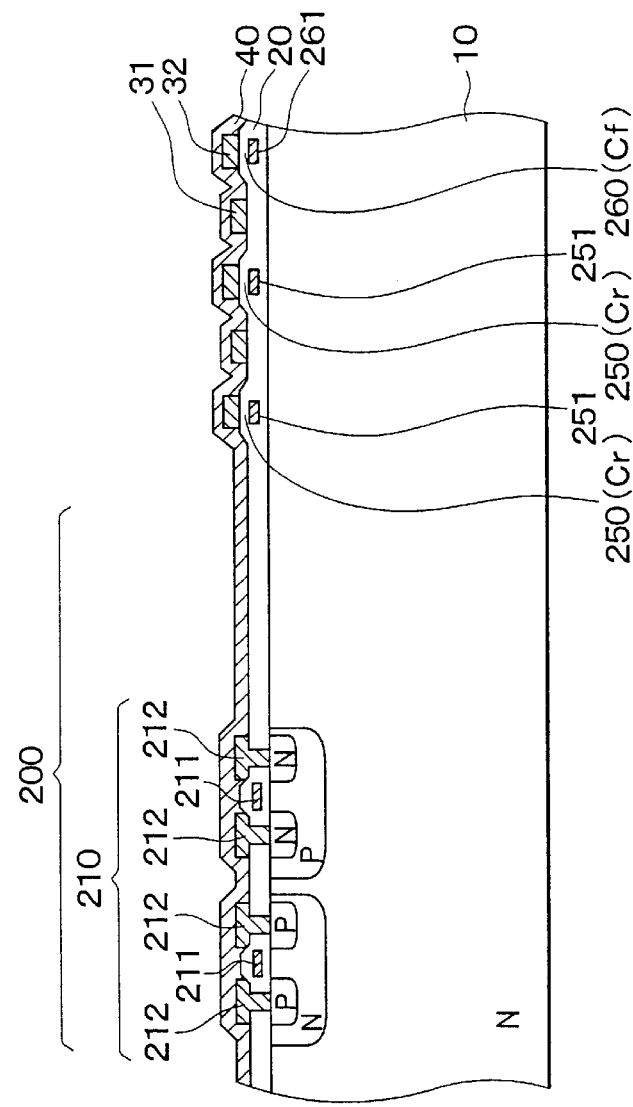

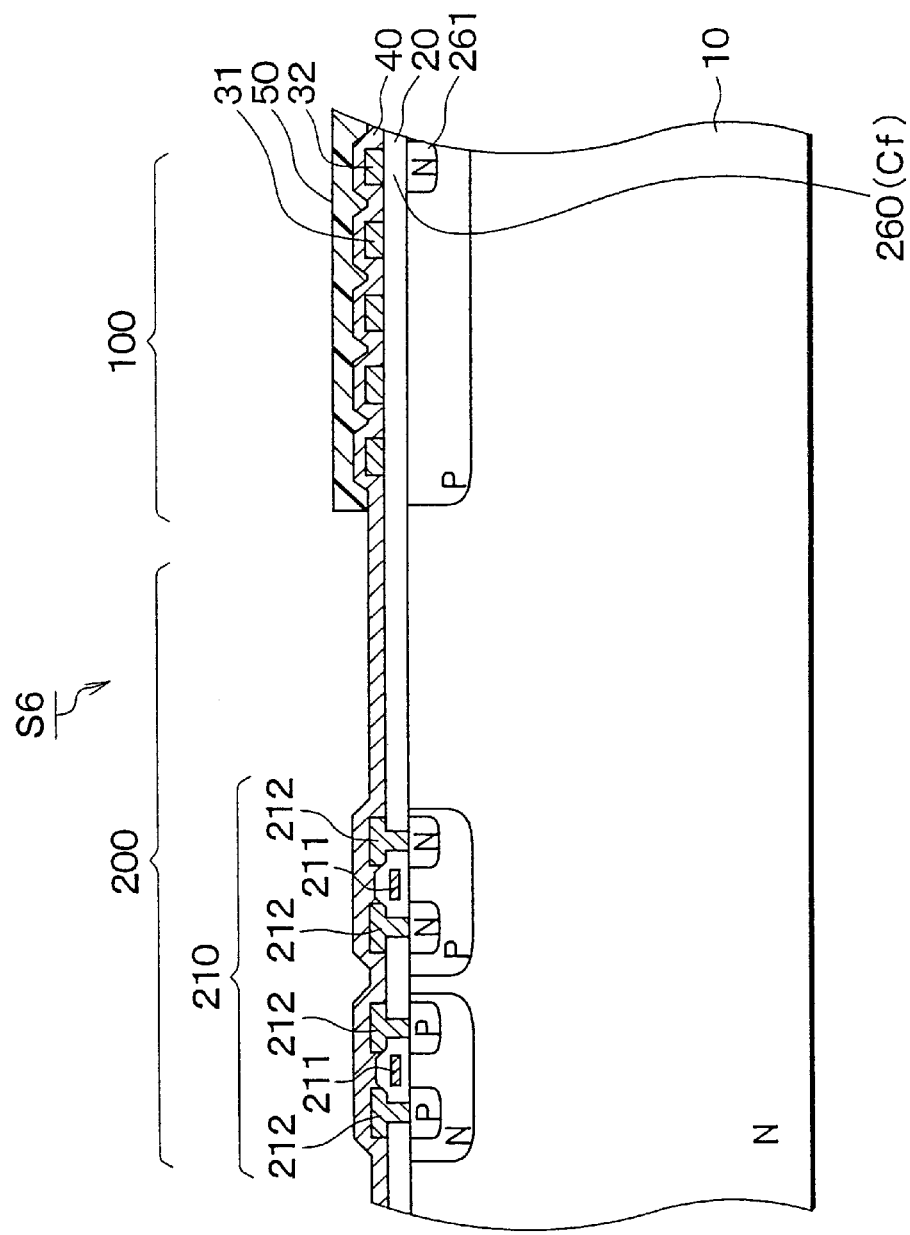

CAPACITIVE HUMIDITY SENSOR

CROSS REFERENCE TO RELATED APPLICATION

This application relates to and incorporates by reference Japanese patent application number 2001-215655, which was filed on Jul. 16, 2001.

BACKGROUND OF THE INVENTION

The present invention relates to a capacitive humidity sensor that has a humidity-sensitive film between a pair of electrodes. The capacitance of the film changes in response to humidity, and the sensor detects humidity by detecting changes in capacitance between the electrodes in correspondence with changes in the surrounding humidity.

A conventional capacitive humidity sensor, in general, includes a semiconductor substrate; a pair of electrodes, which are formed on a surface of the semiconductor substrate and face each other across a distance; and a humidity-sensitive film placed between the electrodes and formed on a surface of the semiconductor substrate. The capacitance of the film changes in response to humidity. The sensor detects humidity by detecting changes in capacitance between the pair of electrodes in response to changes in the surrounding humidity.

Such a capacitive humidity sensor is provided, for example, in Japanese examined patent publication JP-B2-6-105235 and Japanese unexamined patent publications JP-A-55-66749 and JP-A-60-166854. The sensors of these publications include a lower electrode formed on a substrate, a humidity-sensitive film placed on top of the lower electrode, and a thin, humidity-permeating upper electrode on top of the humidity-sensitive film. These sensors are susceptible to problems with reliability and resistance to humidity, however, because the upper electrode is exposed to the outside environment.

SUMMARY OF THE INVENTION

The present invention addresses these issues by providing a capacitive humidity sensor that converts changes in capacitance between a pair of detection electrodes, in response to changes in humidity, into voltage signals using the SC circuits for detection. A first objective of the invention is to keep the sensor small. A second objective is to ensure electrode reliability by preventing the detection electrodes from being exposed to the outside environment.

To achieve these objectives, the invention includes a capacitive humidity sensor, which includes a semiconductor substrate; circuit devices formed on a surface of the semiconductor substrate; a pair of detection electrodes, which are formed on the surface of the semiconductor and oppose each other across a distance; and a humidity-sensitive film, the capacitance of which changes in response to humidity, located between the detection electrodes and formed on the surface of the semiconductor substrate. The capacitance between the detection electrodes changes in response to changes in the surrounding humidity. The circuit devices include switched capacitor circuits having a reference capacitor and a feedback capacitor for converting changes in capacitance between the detection electrodes into voltage signal output. At least one of the reference capacitor and feedback capacitor is an underlying capacitor that is placed beneath a detection electrode.

BRIEF DESCRIPTION OF THE DRAWINGS

FIGS. 4A and 4B are diagrammatic cross sectional views showing sequential steps of the method of manufacturing the capacitive pressure sensor in FIG. 1.

FIG. 11 is a simplified cross sectional view of a capacitive humidity sensor in a fourth example of the third embodiment of the present invention.

DETAILED DESCRIPTION OF THE PREFERRED EMBODIMENTS

First Embodiment

The present invention addresses the problems mentioned above by placing circuit devices for humidity detection on a surface of a semiconductor substrate, integrating a detection part (a pair of detection electrodes and a humidity-sensitive film) with the circuits, and using switched capacitor circuits, suited for detecting minute changes in capacitance with high sensitivity, in a detection circuit.

Figure 3:
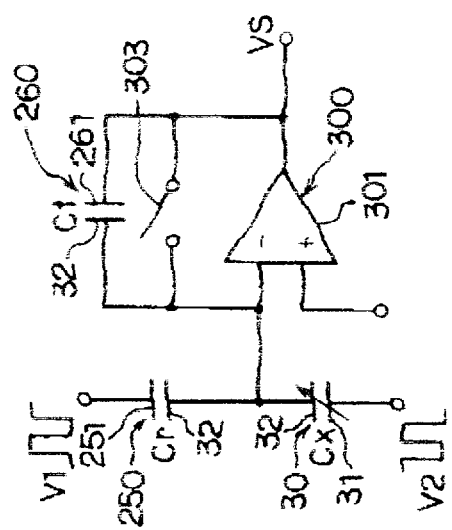
FIG. 3 is a schematic diagram showing the switched capacitor circuits in the capacitive pressure sensor.

The switched capacitor circuits (SC circuits) include a reference capacitor and feedback capacitor for converting changes in capacitance between the detection electrodes into voltage signals. FIG. 3 shows a structure of the detection circuits using the SC circuits.

In FIG. 3, reference number 30 represents a humidity-sensitive capacitor (detection capacitor) having a capacitance Cx formed between a pair of detection electrodes, which face each other across a pressure sensitive film. The capacitance Cx changes in response to the humidity in the surrounding area. Reference number 250 represents a reference capacitor with capacitance Cr. The capacitance Cr does not change in response to changes in humidity in the surrounding area.

Reference number 300 represents a differential amplifier for detecting amid-point potential between the reference capacitor 250 and the humidity-sensitive capacitor 30. The differential amplifier circuits 300 include an operating amplifier 301, a feedback capacitor 260, the capacitance of which is a feedback capacitance Cf, and a switch 303. The feedback capacitor 260 stores charge corresponding to the mid-point potential while the switch 303 is turned on, for integration of signals above the mid-point potential.

Carrier wave signals V1 and V2, which have opposing phases, are fed as inputs into one of the electrodes of the reference capacitor 250 and one of the electrodes of the humidity-sensitive capacitor 30, respectively. The output voltage Vs is an output corresponding to the mid-point potential between the reference and sensing capacitors 250, 30 from the differential amplifier 300. Although the reference capacitance Cr does not change in response to the changes in the surrounding humidity, the variable capacitance Cx does change, and the mid-point potential also changes. For this reason, it is possible to detect the surrounding humidity by detecting the output voltage Vs.

When using the SC circuits, as described above, in a capacitive humidity sensor, it is necessary to create the reference capacitor and the feedback capacitor as a part of the circuit devices on the semiconductor substrate. In order to keep the sensor small, it is desirable to minimize the areas taken up by the detectors and the circuit devices.

Figure 1:
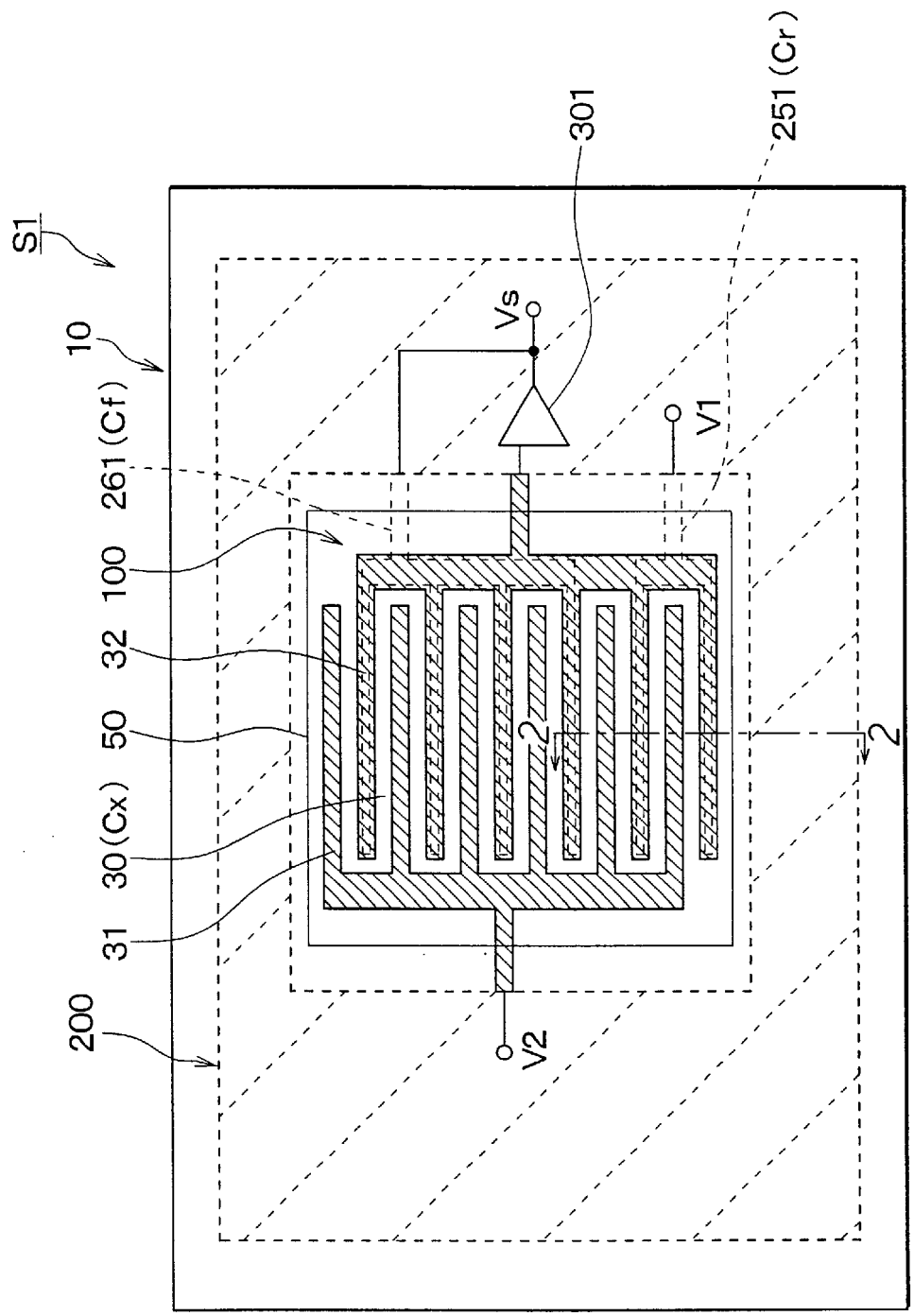
FIG. 1 is a simplified plan view of the capacitive humidity sensor of the first embodiment of the present invention.
Figure 2:
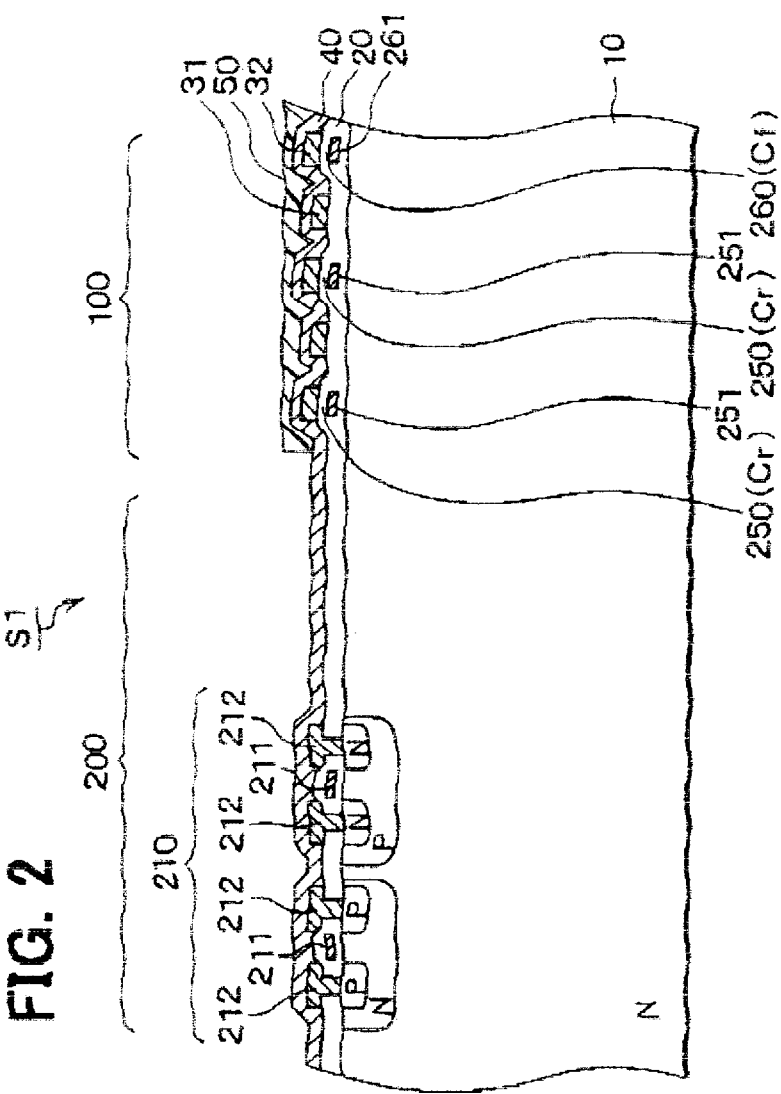
FIG. 2 is a simplified cross sectional view taken along line 2—2 in FIG. 1.

FIGS. 1 and 2 show a capacitive humidity sensor S1 of the first embodiment of the present invention. Some areas in FIG. 1 are shaded for identification, but the shading does not indicate a cross sectional surface. The capacitive humidity sensor S1, for example, is used in a humidity controller in an air conditioner to detect the humidity in a room or for detecting the humidity outdoors for weather forecasting.

Reference number 10 is a semiconductor substrate and is an N-type silicon substrate in this example. A silicon oxide film 20 is formed on the semiconductor substrate 10 as a first insulating film. First and second detection electrodes 31, 32, which are shown as shaded areas in FIG. 11 are formed on the same plane and face each other on the silicon oxide film 20.

As shown in FIG. 1, the detection electrodes 31, 32 in this particular example have flat, comb-like shapes, and the teeth of the two comb-shaped electrodes are interdigitated with one another; however, the shapes of the detection electrodes 31, 32 are not so limited. The comb-shaped electrodes 31, 32 minimize the total size of the areas occupied by the electrodes while maximizing the area across which the detection electrodes 31, 32 face each other, thus maximizing the capacitance between the two electrodes.

The detection electrodes 31, 32 may be made of aluminum, aluminum and silicon (in which a trace amount of silicon (for example, some tenths of a percent) is added to aluminum), titanium, gold, copper, polysilicon, or another material regularly used on a semiconductor production line. In this particular example, the first and second detection electrodes 31, 32 are made of aluminum.

A first electrode 251 of a reference capacitor 250 and a first electrode 261 of a feedback capacitor 260 are buried beneath and face the second detection electrode 32 in the silicon oxide film 20. The first electrodes 251, 261 are made of polysilicon.

As shown with dashed lines in FIG. 1, in this particular example, the first electrodes 251, 261 are comb shaped, when viewed from above, and generally conform to the shape of the corresponding parts of the second detection electrode 32. The first electrodes 251, 261 face the second detection electrode 32 across the silicon oxide film 20 and form capacitors by coupling with the second detection electrode 32.

In other words, the second detection electrode 32 and the first electrode 251 of a reference capacitor 250 face each other to form the reference capacitor 250, which has a capacitance Cr, and the second detection electrode 32 and a first electrode 261 of a feedback capacitor 260 face each other to form the feedback capacitor 260, which has a capacitance Cf. The reference capacitor 250 and the feedback capacitor 260 are underlying capacitors that are formed beneath the detection electrode 32.

The widths of the first electrodes 251, 261 of the capacitors 250 and 260 are preferably less than the width of the detection electrode 32, as shown in FIG. 1. When the first electrodes 251, 261 are wider, the first electrodes 251, 261 can easily form capacitors by coupling with the other detection electrode 31.

A silicon nitride film 40, which forms a second insulating film, is formed above the detection electrodes 31, 32. In this particular example, the silicon nitride film covers the detection electrodes 31, 32 and an area between the detection electrodes 31, 32. However, it is not necessary to have the silicon nitride film 40 cover the area between the detection electrodes 31, 32, as long as the film covers the detection electrodes 31, 32.

A humidity-sensitive film 50, the capacitance of which changes in response to changes in humidity, is formed on the silicon nitride film 40 and covers the electrodes 31, 32 and the area between the electrodes 31, 32.

The humidity-sensitive film 50 may consist of a humidity absorbing organic polymer material. More particularly, polyimide or butyric acid cellulose (polyimide in this particular example) may be used. When water molecules penetrate the humidity-sensitive film 50, the dielectric constant of the film 50 varies. The dielectric constant of the film 50 varies in proportion to the amount of water molecules that penetrate the film 50. As a result, the capacitance between the detection electrodes 31, 32 also changes.

On the semiconductor substrate 10, the area covered by the humidity-sensitive film 50 is a humidity-sensitive area 100. At the humidity-sensitive area 100, the capacitance between the detection electrodes 31, 32 changes in response to changes in the humidity surrounding the sensor S1. Humidity detection is possible based on this change in capacitance.

In this particular embodiment, circuit devices 200, which process signals related to changes in capacitance between the detection electrodes 31, 32 in response to changes in humidity, are located in an area outside of the humidity-sensitive area 100 (at the perimeter of the humidity-sensitive area 100, shown with broken shading lines in FIG. 1) on the surface of the semiconductor substrate 10.

In FIG. 2, the circuit devices 200 are shown as CMOS transistors 210. In the CMOS transistors 210, the reference number 211 represents gate electrodes made of polysilicon, and reference number 212 represents interconnect electrodes that are made of aluminum, which are in contact with sources and drains. Of course, the circuit devices 200 may include other circuit devices (for example, bi-CMOS transistors) in addition to the CMOS transistors 210.

The reference capacitor 250 and feedback capacitor 260 make up a part of the circuit devices 200. With the reference capacitor 250, feedback capacitor 260, and CMOS transistors 210, the circuit devices 200 make up the switched capacitor circuits for converting changes in capacitance between the detection electrodes 31, 32 into voltage signal output.

The switched capacitor circuits (SC circuits) make up the detection circuits of the present sensor S1. The structure and operation of the SC circuits are explained by referring to FIG. 1 and the schematic diagram in FIG. 3.

The humidity-sensitive capacitor (detection capacitor) 30 is formed between the detection electrodes 31, 32 which face each other from opposite ends of the humidity-sensitive film 50. The capacitance Cx of the humidity-sensitive capacitor 30 changes in response to changes in humidity. On the other hand, the capacitance Cr of the reference capacitor 250 does not change, even when the humidity in the surrounding area changes.

A differential amplifier 300 detects a mid-point potential between the reference capacitor 250 and the humidity-sensitive capacitor 30 and includes an op amp 301 made of the CMOS transistors 210. The differential amplifier 300 includes a feedback capacitor 260, the capacitance of which is Cf, and a switch 303.

Carrier wave signals V1 and V2, the phases of which oppose each other, are input to one of the electrodes of the reference capacitor 250 (reference capacitor opposing electrode 251) and one of the electrodes of the humidity-sensitive capacitor 30 (a detection electrode 31), respectively, and the mid-point potential between the two capacitors 250 and 30 is provided as an output voltage Vs through the differential amplifier 300. While the reference capacitance Cr remains constant, the variable capacitance Cx changes in response to changes in the surrounding humidity, and the mid-point potential also changes. For this reason, it is possible to detect humidity by detecting the output voltage Vs.

As discussed thus far, the present embodiment provides SC circuits for humidity detection that include the first electrode 251 of the reference capacitor 250 and the first electrode 261 of the feedback capacitor 260, which are formed beneath the detection electrode 32. The detection electrode 32 is one of the detection electrodes 31, 32 and is connected to the op amp 301. The reference capacitor 250 and the feedback capacitor 260 are formed beneath the detection electrode 32.

A method of manufacturing the capacitive humidity sensor S1 in this embodiment will be explained by referring to FIGS. 4A and 4B. FIG. 4A and FIG. 4B show cross sectional views, corresponding to FIG. 2, for the process steps in this method of manufacturing.

Steps Shown in FIG. 4A

Firstly, a diffusion layer and a thermal oxide film 21, that make up the circuit devices 200, are formed on a surface of the semiconductor substrate 10 by regular ion implanting and thermal diffusion steps. Then, the electrodes 211, 251, 261, which are made of polysilicon, are formed by CVD, and diffusion areas for source and drain in the MOS transistors 210 are formed by regular ion implanting and thermal diffusion steps. These steps are shown in FIG. 4A.

Steps Shown in FIG. 4B

A silicon oxide film 20 is formed by CVD. At the same time, the silicon oxide film and the thermal oxide film 21, mentioned above, merge into one to form the silicon oxide film 20, which is the first insulating film. As a result, the opposing electrodes 251, 261 are buried in the silicon oxide film 20.

Furthermore, contact holes, for establishing contact between the circuit devices 200 and interconnect electrodes for the circuit devices 200 on the semiconductor substrate 10, are formed by photolithography and etching on the silicon oxide film 20.

Interconnect electrodes for the circuit devices 200 (only the interconnect electrodes 212 are shown) and the detection electrodes 31, 32 are formed with aluminum by sputtering or vapor deposition. Then a silicon nitride film (second insulating film) 40 is deposited on top by plasma CVD. These steps are shown in FIG. 4B.

Although not shown in the figures, the silicon nitride film 40 is stripped by photolithography and etching to form pads for establishing contact with the circuit devices 200 from the outside. These areas, where the silicon nitride film 40 is stripped, become pads.

Finally, a humidity-sensitive film 50 is formed on top of the silicon nitride film 40 by a method in which a polyimide film is spin coated, cured, and photo etched or a method in which a polyimide film is printed and cured. Using the manufacturing method described thus far, the capacitive humidity sensor S1 shown in FIG. 2 can be manufactured on a normal semiconductor production line.

In the present embodiment, the detection electrodes 31, 32 are formed on top of the silicon oxide film (first insulating film) 20 to face each other and in isolation from each other, so that the detection electrodes 31, 32 are insulated from each other.

Because the silicon nitride film (second insulating film) 40 is placed between the detection electrodes 31, 32 and the humidity-sensitive film 50, the detection electrodes 31, 32 are covered by the silicon nitride film 40 and are not exposed to the environment. The reliability of the detection electrodes 31, 32 is thus ensured.

Furthermore, in the present embodiment, the reference capacitor 250 and feedback capacitor 260, which make up the SC circuits, are formed beneath the detection electrode 32, which connects to the differential amplifier 300 (op amp 301) of the SC circuits.

If the first detection electrode 31, instead of the second detection electrode 32 that is connected to the differential amplifier 300 (op amp 301), then the capacitors 250, 261 should be formed beneath the first detection electrode 31, and the carrier wave signals V2 should be fed to the second detection electrode 32.

By forming the reference capacitor 250 and feedback capacitor 260 beneath the detection electrode 31 or 32, it is possible to implement the SC circuits shown in FIG. 3. Because the capacitors 250 and 260 and the humidity-sensitive part 100 are stacked on top of each other, the device surface area can be minimized.

This embodiment, therefore, makes it possible to limit the size of the capacitive humidity sensor while keeping the detection electrodes 31, 32 from being exposed to the outside environment, which ensures the reliability and resistance to moisture of the electrodes 31, 32.

Furthermore, in this embodiment, the first electrodes 251, 261 for the reference capacitor 250 and feedback capacitor 260 are made of polysilicon, and the gate electrodes 211 of the MOS transistors 210 for the SC circuits in the circuit devices 200 are also made of polysilicon.

Because the first electrodes 251, 261 and gate electrodes 211 are made of the same material, as shown in the method of manufacturing described above, the gate electrodes 211 for the MOS transistors 210 and the first electrodes 251, 261 for the reference capacitor 250 and feedback capacitor 260 can be formed simultaneously with polysilicon using a CVD method or other methods on the surface of the semiconductor substrate 10, which simplifies the manufacturing process.

Because the present embodiment ensures resistance to moisture for the detection electrodes 31, 32, it is not necessary to use specialized metal materials that would resist moisture, such as a noble metal, for the detection electrodes 31, 32. Materials regularly used on a normal semiconductor production line (for example, aluminum) may be used instead. Therefore, the present sensor S1 can be manufactured at low cost using a high volume semiconductor process to limit size.

Furthermore, because the steps leading up to the deposition of the humidity-sensitive film 50 are based on a regular semiconductor manufacturing process, high density, fine geometry and low cost processing is possible in the processes, including the process of forming the detection electrodes 31, 32. The polyimide material used as the humidity-sensitive film in this example is also a material regularly used in a normal semiconductor process as a passivation film and is highly compatible with a semiconductor process.

In the present embodiment, the circuit devices 200 and the detection electrodes 31, 32 are integrated on the same semiconductor substrate 10. As a result, it is possible to make the floating capacitance, which exists between the circuit devices 200 and the detection electrodes 31, 32, small. Because the surface areas taken up by the detection electrodes 31, 32 can be made smaller, it is possible to provide a small capacitive humidity sensor.

In the present embodiment, the humidity-sensitive film 50 may be of a moisture absorbent organic polymer material. In particular, a material that can be coated and cured at less than 400° C. would be desirable. A curing temperature of less than 400° C. would not have an adverse effect on the semiconductor devices. For example, some polyimide materials can be cured at approximately 350° C.

In the present embodiment, the material used for the detection electrodes 31, 32 should preferably be the same as the interconnect material used for the interconnect electrodes 212 for the circuit devices 200. A resulting manufacturing process will be more efficient, because the interconnect electrodes for the circuit devices 200 and the detection electrodes 31, 32 can be manufactured in the same step.

For example, if the interconnect electrodes for the circuit devices 200 and the detection electrodes 31, 32 were formed using aluminum by sputtering or vapor deposition, the number of process steps could be reduced in the manufacturing process described above. In addition, the detection electrodes 31, 32 will not require a separate mask.

Furthermore, the second insulating film that covers the detection electrodes 31, 32 can consist of an insulating material other than silicon nitride (for example, silicon oxide). In the present embodiment, however, the silicon nitride film 40 is used. The silicon nitride film 40 has a relatively high dielectric constant for an insulating material and helps maximize capacitance between the detection electrodes 31, 32 and helps improve the detection sensitivity.

Although the first insulating film between the semiconductor substrate 10 and the detection electrodes 31, 32 can be an insulating material other than silicon oxide (for example, a silicon nitride film), the silicon oxide film 20, which has a dielectric constant lower than silicon nitride film, is used in this embodiment. As a result, parasitic capacitance between the semiconductor substrate 10 and the detection electrodes 31, 32 is minimized, and detection sensitivity is enhanced.

Second Embodiment

Figure 5:
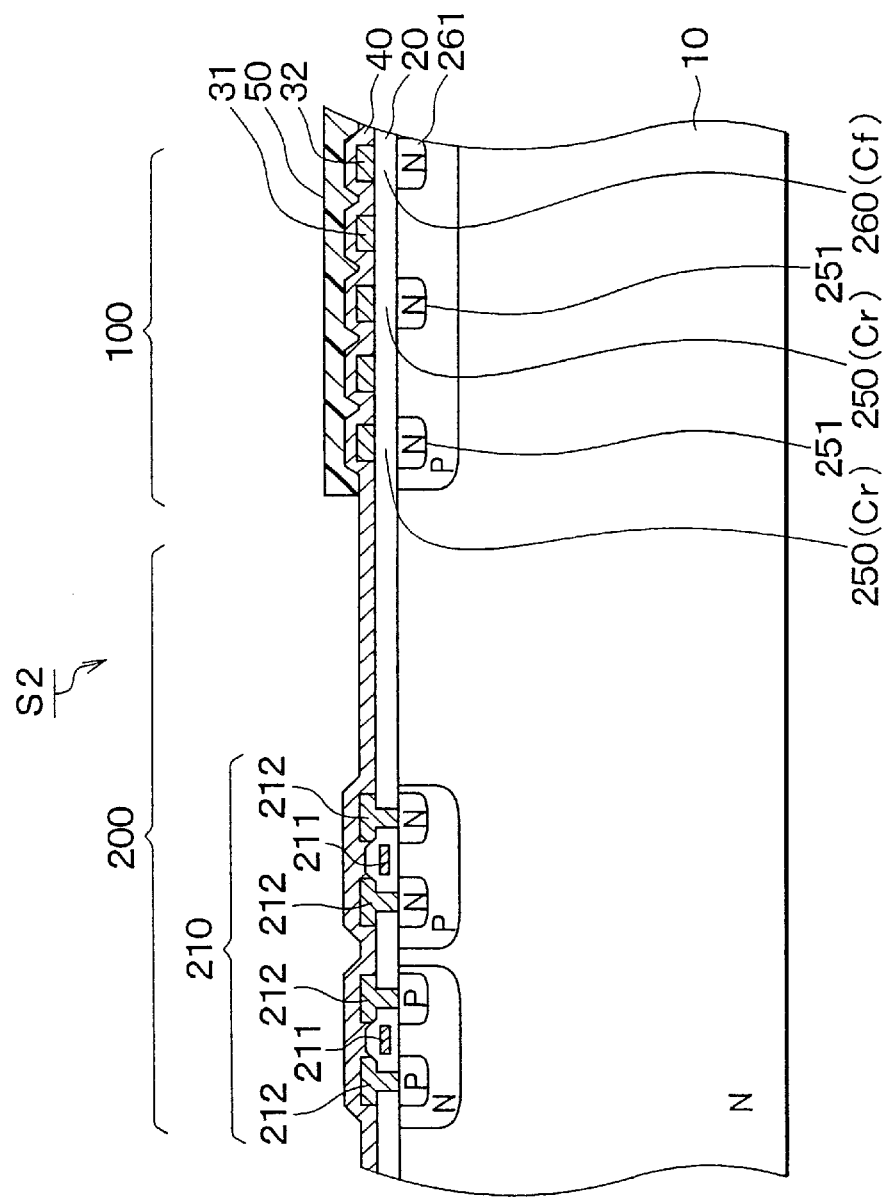
FIG. 5 is a simplified cross sectional view of the capacitive humidity sensor of a second embodiment of the present invention.

A simplified cross sectional view of a capacitive humidity sensor S2 of the second embodiment of the present invention is shown in FIG. 5. The second embodiment is different from the first embodiment in that the first electrodes 251, 261 for the reference capacitor 250 and the feedback capacitor 260 are formed with a diffusion layer (an N-type layer in this drawing), formed on the surface of the semiconductor substrate 10, instead of polysilicon.

The opposing electrodes 251, 261 made of the diffusion layer are located beneath the detection electrode 32 and face the detection electrode 32 across the silicon oxide film 20 to form capacitors 250 and 260, respectively.

If the first electrodes 251, 261 have the same impurity concentration profile as the diffusion layer used for the circuit devices 200, the opposing electrodes 251, 261 may be formed at the same time as the diffusion layer for the circuit devices 200 using a normal ion implanting and thermal diffusion method as in the step shown in the FIG. 4A. As a result, the manufacturing process would be simplified.

Comparing the first embodiment and the second embodiment, the device of the first embodiment is larger, because the opposing electrodes 251, 261 are buried in the silicon oxide film 20 under the detection electrode 32, and the silicon oxide film 20 between the detection electrode 32 and the opposing electrodes 251, 261 is thinner.

Unlike the second embodiment, in which the electrical isolation of the opposing electrodes 251, 261 is ensured with PN junctions, the first embodiment relies on the silicon oxide film 20 for a more reliable electrical isolation of the opposing electrodes.

Third Embodiment

Although, in the first and second embodiments, both the reference capacitor 250 and the feedback capacitor 260 are placed beneath the detection electrode 32, which is a part of the detection electrodes 31, 32, it is also possible to reduce the size of the device area by placing only one of the capacitors 250 and 260 beneath the detection electrodes 31, 32. FIG. 6 to FIG. 11 show various examples of the third embodiment.

Figure 6:
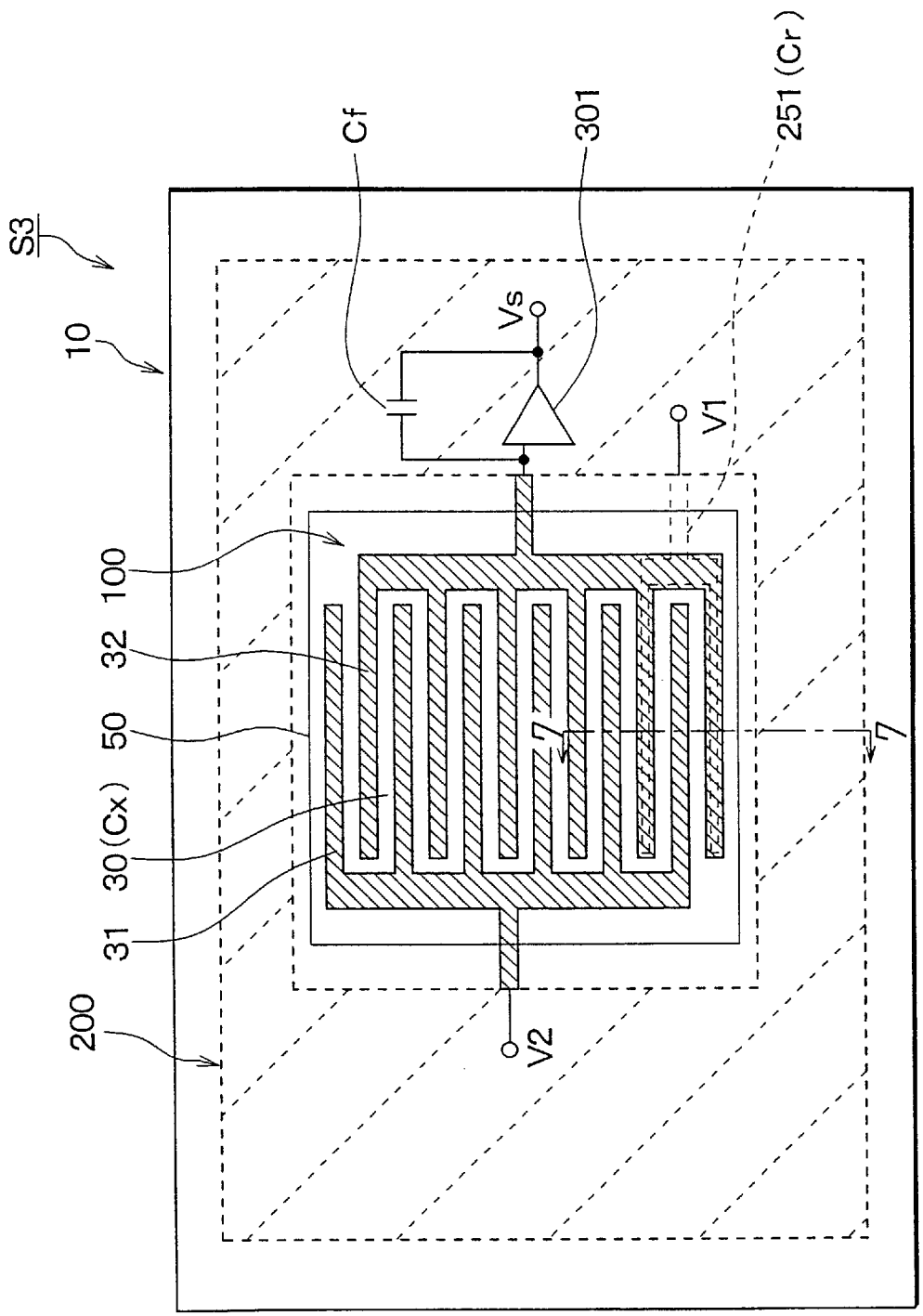
FIG. 6 is a simplified plan view of the capacitive humidity sensor in a first example of a third embodiment of the present invention.
Figure 7:
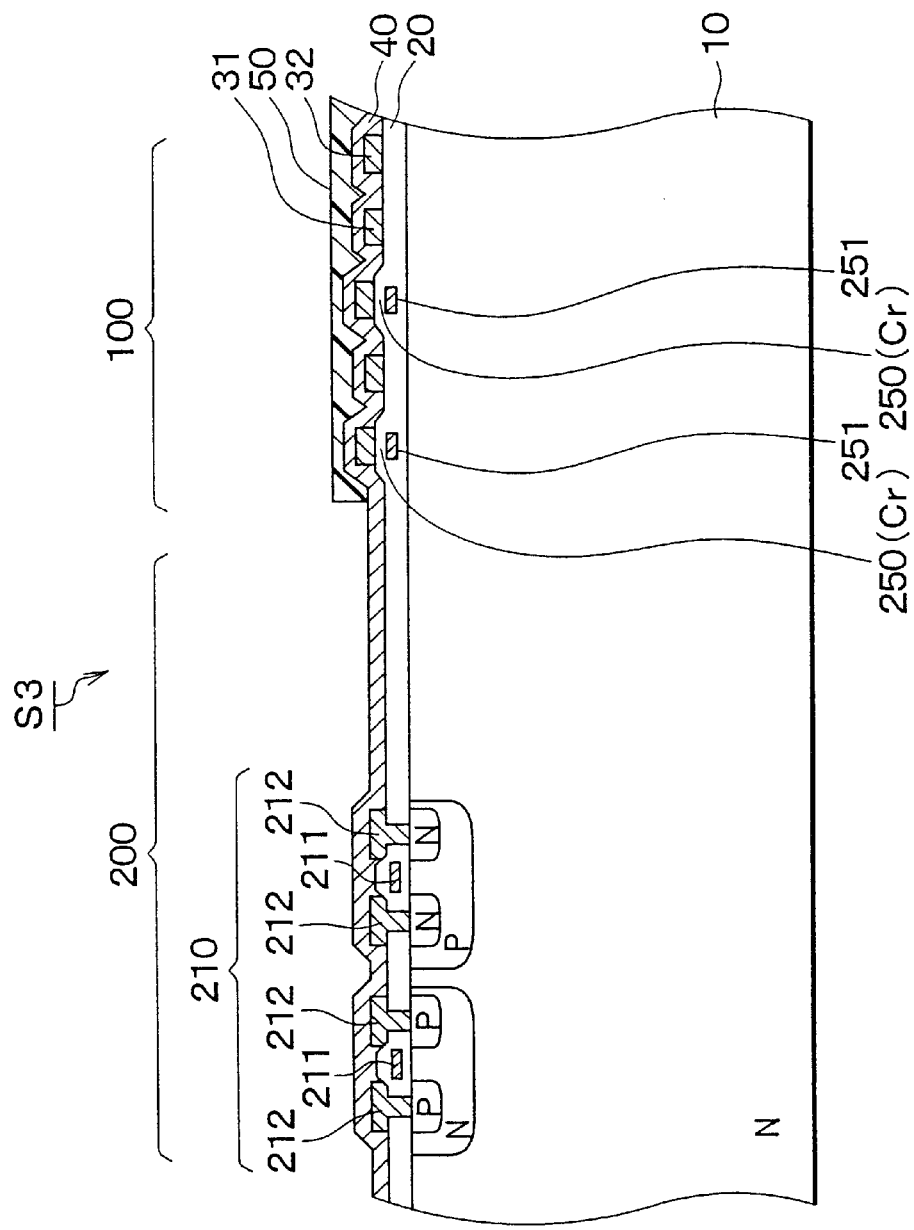
FIG. 7 is a simplified cross sectional view taken along line 7—7 in FIG. 6.

FIGS. 6 and 7 show a simplified top view of a capacitive humidity sensor S3 as a first example of the present embodiment. In this first example, only the reference capacitor 250, that is, the first electrode 251 of the reference capacitor 250, which is made of polysilicon, is placed beneath the second detection electrode 32. In this instance, the feedback capacitor is formed using a regular MOS capacitor within the circuit devices 200.

Figure 8:
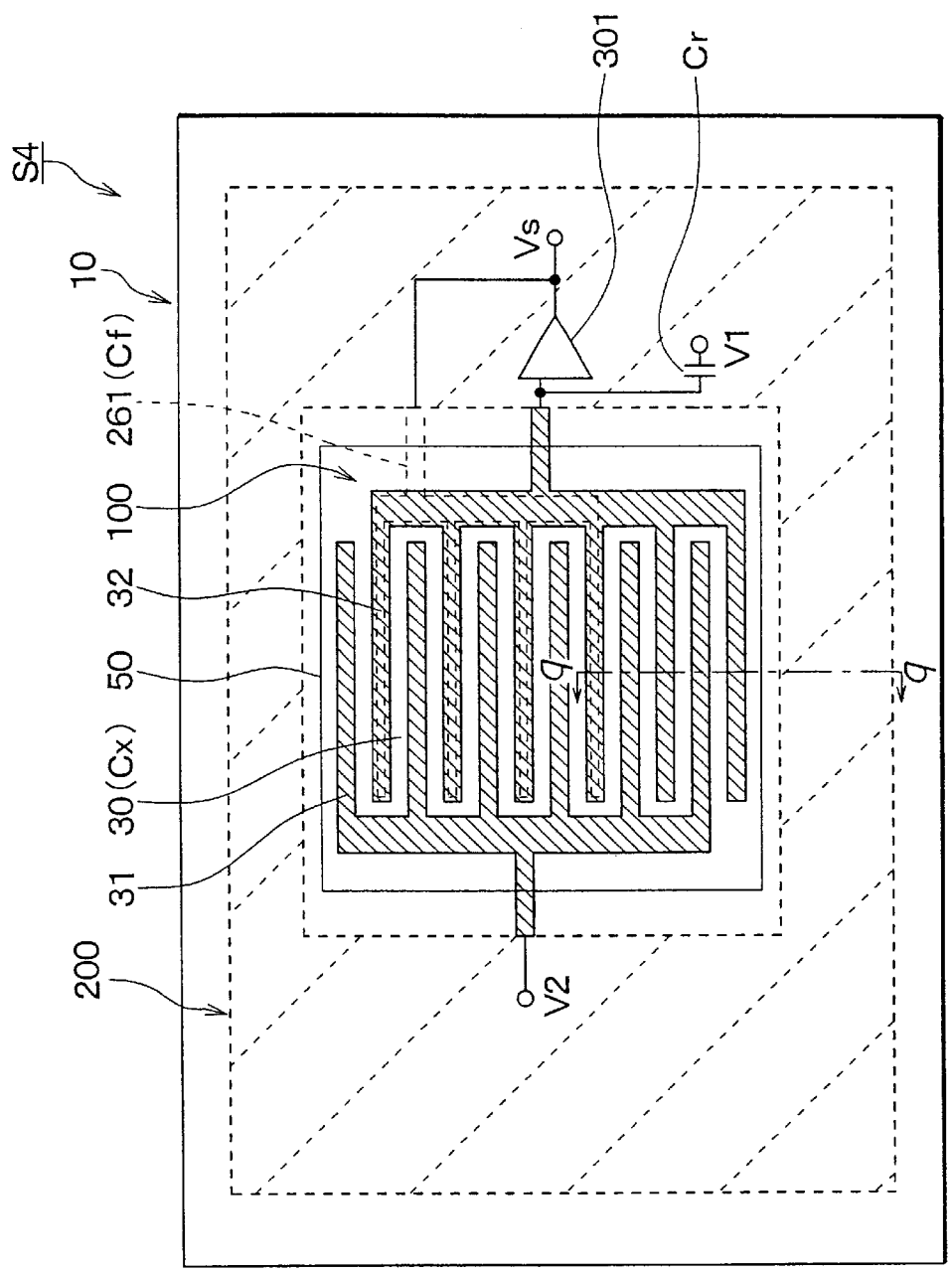
FIG. 8 is a simplified top view of the capacitive humidity sensor in a second example of the third embodiment of the present invention.
Figure 9:
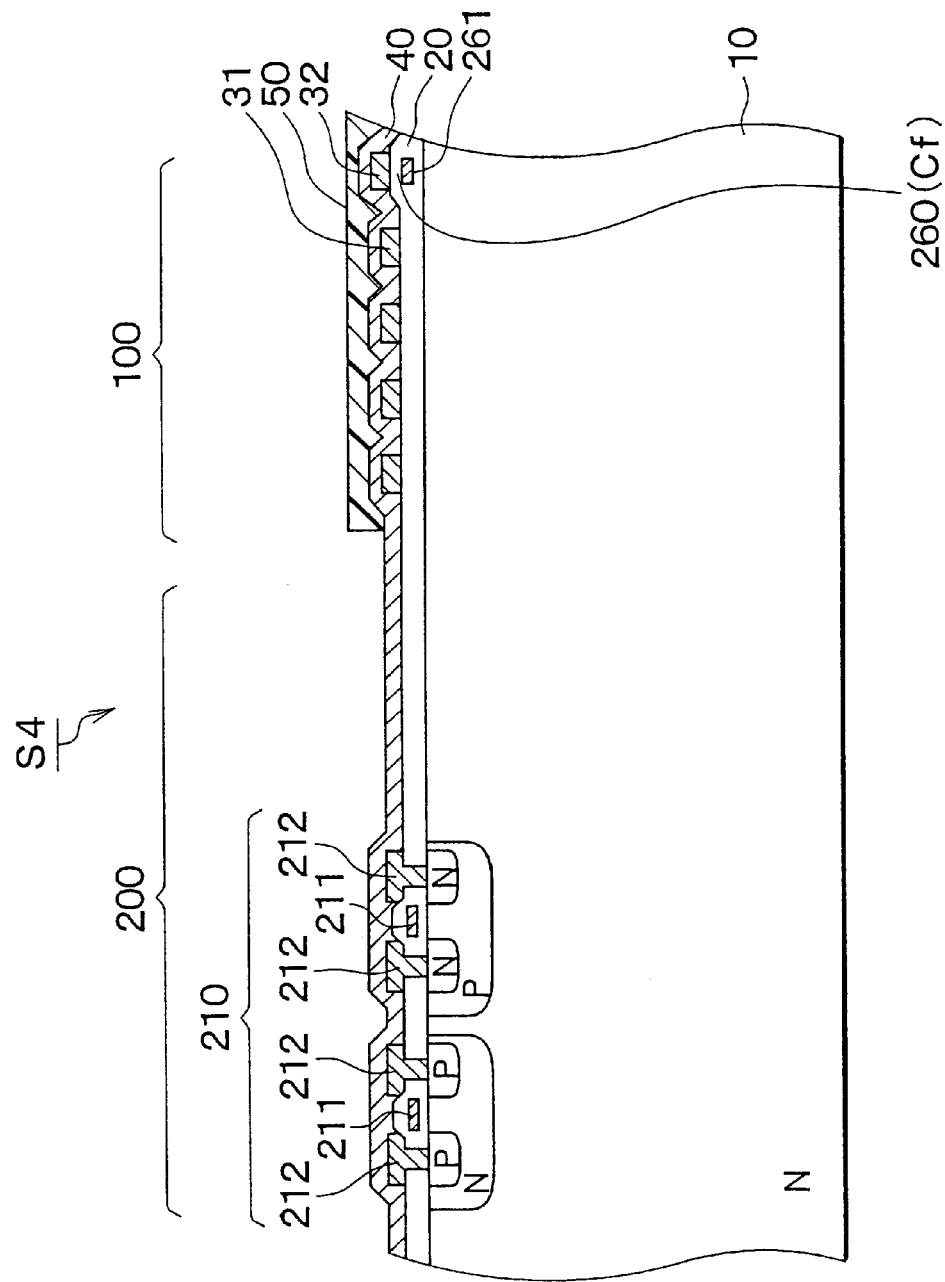
FIG. 9 is a simplified cross sectional view taken along line 9—9 in FIG. 8.

FIG. 8 and FIG. 9 show a parasitic capacitive humidity sensor S4 as a second example of the third embodiment. In this example, only the feedback capacitor 260 is placed beneath the second detection electrode 32. That is, first electrode 261, which is made of polysilicon, of the feedback capacitor is placed beneath the second detection electrode 32. In this instance, the reference capacitor is formed using a regular MOS capacitor within the circuit devices 200.

Figure 10:
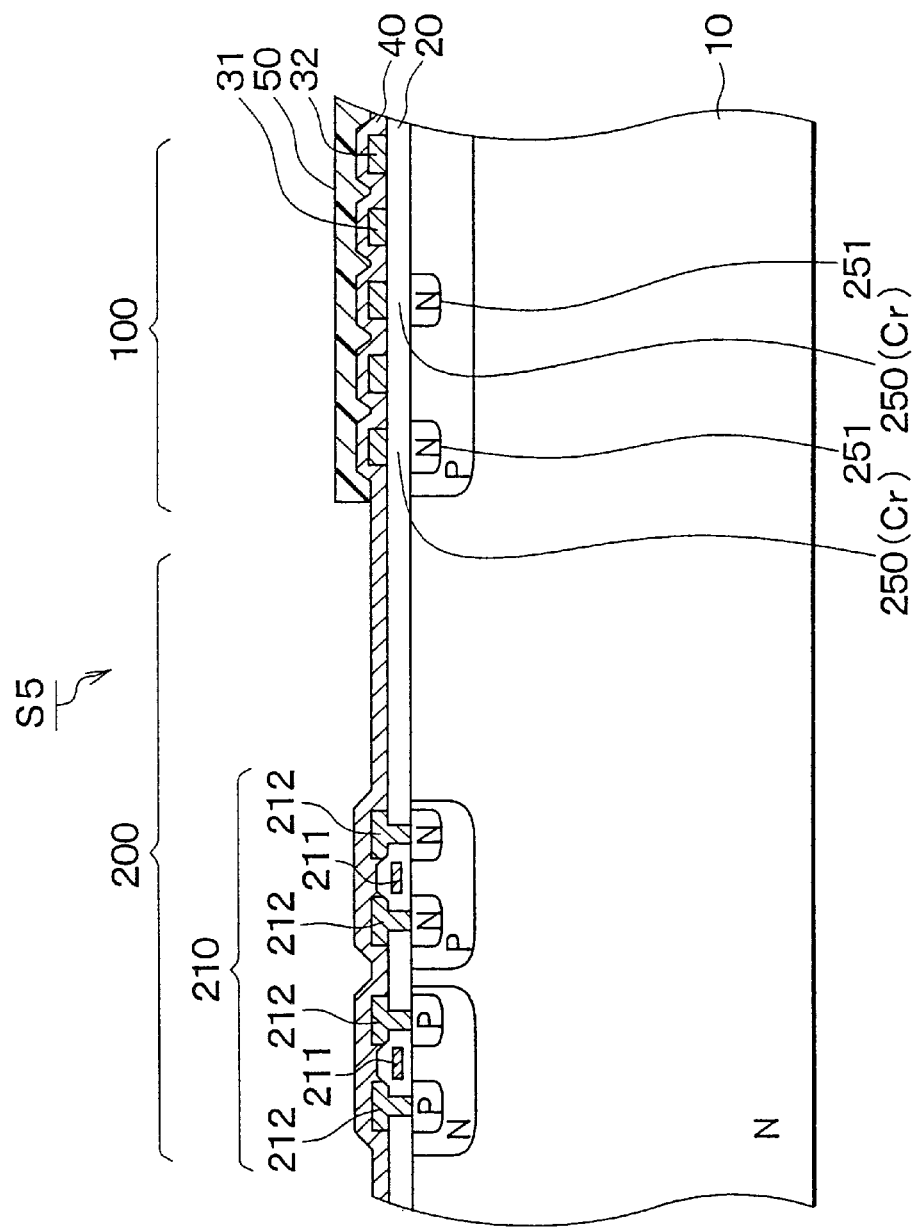
FIG. 10 is a simplified cross sectional view of the capacitive humidity sensor in a third example of the third embodiment of the present invention.

Furthermore, FIG. 10 shows a third example of the third embodiment. In this example, only the reference capacitor 250 is placed beneath the second detection electrode 32. That is, the first electrode 251, which is made of an n-type diffusion layer, of the reference capacitor is placed beneath the second detection electrode 32.

Furthermore, FIG. 11 shows a fourth example of the third embodiment. In this example, only the feedback capacitor 260 is placed beneath the detection electrode 32. That is, the first electrode 261, which is made of an n-type diffusion layer, of the feedback capacitor is placed beneath the detection electrode 32.

Even in the examples of the third embodiment, the device surface area is reduced compared with a device in which both the reference capacitor 250 and the feedback capacitor 260 are formed on the semiconductor substrate 10.

Other Embodiments

In the present invention, it is also possible to have one of the detection electrodes placed beneath the humidity-sensitive film and the other electrode above the humidity-sensitive film, as in the capacitive humidity sensor provided in the publications mentioned earlier. In such an instance, the reference capacitor and feedback capacitor can be formed beneath an electrode for detection by placing the opposing electrodes mentioned above across an insulating film underneath the electrode for detection, which is placed beneath the humidity-sensitive film.

In essence, the present invention provides a capacitive humidity sensor that includes a semiconductor substrate, circuit devices formed on a surface of the semiconductor substrate, a pair of detection electrodes that are isolated from each other and facing each other and formed on the surface of the semiconductor substrate, and a humidity-sensitive film, the capacitance of which changes in response to humidity and placed between the detection electrodes and formed on the surface of the semiconductor substrate. The capacitance between the detection electrodes changes in response to changes in the surrounding humidity in this capacitive humidity sensor. The circuit devices include switched capacitor circuits that include a reference capacitor and a feedback capacitor for converting changes in capacitance between the detection electrodes into voltage signal output in this capacitive sensitive pressure. Furthermore, at least one of the reference capacitor and the feedback capacitor is placed beneath the electrode for detection. Other details may be changed.

I claim:

1. A capacitive humidity sensor comprising:
   a semiconductor substrate;
   circuit devices formed on a surface of the semiconductor substrate;
   two detection electrodes, which are isolated from one another and are opposed to one other, wherein the detection electrodes are formed on the surface of the semiconductor substrate; and
   a humidity-sensitive film, the capacitance of which changes in response to humidity, placed between the detection electrodes and formed on the surface of the semiconductor substrate, wherein:
      the capacitance between the detection electrodes changes in response to changes in the surrounding humidity;
      the circuit devices make up switched capacitor circuits comprising a reference capacitor and feedback capacitor that convert changes in capacitance between the detection electrodes into voltage signal output; and
      at least one of the reference capacitor and the feedback capacitor is an underlying capacitor and is located beneath one of the detection electrodes.

2. The capacitive humidity sensor of claim 1, further comprising an insulating film, wherein the underlying capacitor is formed by forming one electrode of the underlying capacitor beneath the one electrode for detection such that the one electrode of the underlying capacitor faces the one detection electrode across an insulating film.

3. The capacitive humidity sensor of claim 2, wherein the one electrode of the underlying capacitor is made of polysilicon.

4. The sensor of claim 3, wherein the circuit devices comprise:
   MOS transistors, which are parts of the switched capacitor circuits; and
   gate electrodes, wherein the gate electrodes include polysilicon.

5. The capacitive humidity sensor of claim 2, wherein the one electrode of the underlying capacitor is formed with a diffusion layer that is formed at the surface of the semiconductor substrate.

6. The capacitive humidity sensor of claim 1, wherein each of the detection electrodes is comb shaped and has tooth like parts, and the tooth-like parts of one of the detection electrodes are interdigitated with the tooth-like parts of the other detection electrode.

7. A capacitive humidity sensor comprising:
   a semiconductor substrate;
   circuit devices formed on a surface of the semiconductor substrate;
   a first insulating film formed on the surface of the semiconductor substrate;
   two detection electrodes formed in isolation from each other and opposed to each other on the first insulating film;
   a second insulating film formed to cover the detection electrodes; and
   a humidity-sensitive film, the capacitance of which changes in response to humidity, formed on the second insulating film to cover the detection electrodes and an area between the detection electrodes, wherein:
      the capacitance between the detection electrodes changes in response to changes in surrounding humidity;
      the circuit devices make up switched capacitor circuits comprising a reference capacitor and a feedback capacitor for converting changes in capacitance between the detection electrodes into voltage signal output; and
      at least one of the reference capacitor and the feedback capacitor is an underlying capacitor that is formed beneath one of the detection electrodes.

8. The capacitive humidity sensor of claim 7, wherein the underlying capacitor is formed by forming an electrode of the underlying capacitor beneath the one detection electrode such that the electrode of the underlying capacitor faces the one detection electrode across the first insulating film.

9. The capacitive humidity sensor of claim 8, wherein the one electrode of the underlying capacitor is made of polysilicon.

10. The sensor of claim 9, wherein the circuit devices comprise:
    MOS transistors, which are parts of the switched capacitor circuits; and
    gate electrodes, wherein the gate electrodes include polysilicon.

11. The capacitive humidity sensor of claim 8, wherein the one electrode of the underlying capacitor is formed with a diffusion layer that is formed at the surface of the semiconductor substrate.

12. The capacitive humidity sensor of claim 7, wherein each of the detection electrodes is comb shaped and has tooth like parts, and the tooth-like parts of one of the detection electrodes are interdigitated with the tooth-like parts of the other detection electrode.

* * * * *